United States Patent [19]

Satake et al.

[11] Patent Number: 4,540,286
[45] Date of Patent: Sep. 10, 1985

[54] APPARATUS FOR CONTINUOUSLY MEASURING THE DEGREE OF MILLING OF GRAINS

[75] Inventors: Toshihiko Satake; Yukio Hosaka, both of Higashihiroshima, Japan

[73] Assignee: Satake Engineering Co., Ltd., Tokyo, Japan

[21] Appl. No.: 486,808

[22] Filed: Apr. 19, 1983

[30] Foreign Application Priority Data

Jun. 3, 1982 [JP] Japan .................................. 57-94063
Jul. 6, 1982 [JP] Japan ................................ 57-116175

[51] Int. Cl.³ ...................... G01N 21/47; G01N 21/13
[52] U.S. Cl. ...................................... 356/445; 99/488; 356/73
[58] Field of Search ............... 356/445, 446, 447, 448, 356/237, 239, 73, 402, 429, 432, 36; 364/734; 99/488, 600, 609, 519

[56] References Cited

U.S. PATENT DOCUMENTS 3,446,299 5/1969 Leonowicz ...................... 364/734 X
3,827,808 8/1974 Cho ..................................... 356/429
4,259,020 3/1981 Babb ................................... 356/402

FOREIGN PATENT DOCUMENTS 0030641 2/1983 Japan ................................... 356/432

Primary Examiner—Vincent P. McGraw
Assistant Examiner—Robert D. V. Thompson, III
Attorney, Agent, or Firm—Wegner & Brestchneider

[57] ABSTRACT

An apparatus for continuously measuring the degree of milling of rice grains wherein there is provided a grain passage unit, one wall of which is positioned angularly so that the grains in contact therewith slide down with their lengthwise axes generally parallel to this wall and another wall of which is positioned so that the grains introduced in the grain passage unit flow without a gap between this wall and the grains, and wherein there are provided integrated data take-up units, the inputs of which are connected to amplifiers and the outputs of which are coupled to a degree of milling meter through an arithmetic unit so that the integrated data obtained in a given period divided into a number of divisions is averaged to calculate the degree of milling sought.

4 Claims, 4 Drawing Figures

APPARATUS FOR CONTINUOUSLY MEASURING THE DEGREE OF MILLING OF GRAINS

BACKGROUND OF THE INVENTION

The present invention relates to an apparatus for continuously measuring the degree of milling of grains, typically of rice grains.

Generally, rice grains are milled by use of a whitening machine to remove bran thereby increasing the degree of whiteness of the rice grains. Conventionally, the grades of this whiteness have been noted as an indication of the degree of milling of rice grains. In the conventional devices for measuring the degree of whiteness, a tray on which the grains to be inspected are placed is positioned at the lower portion of an integrating sphere formed with an inner mirror surface, the grains are illuminated from an upper part of the integrating sphere by light transmitted through an infrared filter and a monochromatic light filter and condensed by a condenser lens, and the reflected light from the grains is collected at a light receiving element disposed at a side portion of the integrating sphere. The current generated by the reflected light receiving element is amplified by an amplifier and measured as the degree of whiteness of the grains.

There are two types of rice whitening machines, one being of a grinding type and the other being of a friction type. When the milled rice grains are examined with the unaided eye, those well milled by the friction type machine are found to be superior in their translucency and polish to those well milled by the grinding type machine. This results from the fact that, whereas the grains milled with the grinding type apparatus have scarred and rough surfaces due to the grinding action of the grinding roll against the grains, the surfaces of those milled with the friction type machines are smooth because the milled is effected by the mutual rubbing action between the grains being milled.

In the conventional degree of whiteness measuring apparatus, since the light reflected from the grains is measured and used as the degree of whiteness, there is a tendency that the grains with rougher surfaces which produce a greater diffused reflection indicate a higher degree of whiteness than the grains with smoother surfaces even if both the grains have the same degree of milling. This is because the amount of the light transmitted through the grains with smoother surfaces is greater than the amount of the light transmitted by the grains with rougher surfaces. Thus, with the conventional method of measuring the degree of milling which is based on the degree of whiteness, it is not possible to accurately determine the value of the degree of milling because the smoother the surfaces become the greater the light transmission ratio is as compared with the light reflection ratio.

Noting the above problem, we have previously proposed and disclosed in Japanese Unexamined Patent Publication No. 77637/83 laid open May 11, 1983, an apparatus for continuously measuring the degree of milling of rice grains with an improved accuracy, in which the degree of milling was measured based not only on the light reflected from but also on the light transmitted through the grains and the degree of milling was obtained based on both the factors. This apparatus enabled continuous measurement of grains by making the grains flow through a grain passage unit and the degree of milling was continuously measured there.

However, in the previous apparatus, since the grain passage unit included a vertical passage way, the grains flowed through the passage way in disorderly and irregular manner and thus because of irregularities and inconsistencies in the value of the reflected light it was not always possible to obtain an accurate value for the degree of milling.

The previous apparatus referred to in the foregoing in which the value calculated in an arithmetic unit based on the amount of the reflected light and the amount of the transmitted light was used directly as the degree of milling had a drawback in terms of reliability of the measured data, the drawback stemming from the fact that each measurement was for each given time of calculation, since the amount of reflected light from a reflected light detecting unit and the amount of the transmitted light from a transmitted light detecting unit change from time to time as shown in FIG. 4 and may be affected by various conditions such as the variation in the amount of grains fed at any one given time.

One object of the present invention is to provide an improved apparatus for continuously measuring the degree of milling of rice grains by which a more accurate value of the degree of milling can be obtained by positioning the grain passage at an appropriate angle to make the grains flow in the best condition.

To this end, the present invention provides an apparatus for continuously measuring the degree of milling of rice grains including a light source unit, a grain passage unit, a reflected light detecting unit, a transmitted light detecting unit, an arithmetic unit and a degree of milling meter wherein one wall of the grain passage unit is positioned angularly so that grains in contact with the wall slide down with their lengthwise axes oriented generally parallel to the wall surface and another wall is positioned so that the grains introduced and filled in the grain passage unit flow without a gap between this wall and the grains.

Another object of the present invention is to provide a further improved apparatus for continuously measuring the degree of milling of rice grains which diminishes irregularities in the measured values and in which the integrated value of the degree of milling is obtained by having the continuously flowing grains measured over a given period which period is divided into as many as several tens or several hundreds of divisions and the integrated data thus obtained is averaged to calculate the degree of milling being sought.

Thus, the present invention also provides an apparatus for continuously measuring the degree of milling of rice grains including a light source unit, a grain passage unit, a reflected light detecting unit, a transmitted light detecting unit, an arithmetic unit, a degree of milling meter, a first integrated data take-up unit and a second integrated data take-up unit wherein the first integrated data take-up unit and the second integrated data take-up unit are connected to the degree of milling meter through the arithmetic unit, so that the integrated data obtained in a given period divided into a number of divisions is averaged to calculate the degree of milling being sought.

BRIEF DESCRIPTION OF THE DRAWINGS

The foregoing objects and advantages of the invention will become more apparent from the following description of preferred embodiments of the invention as applied to an apparatus for continuously measuring the degree of milling of rice grains in conjunction with the attached drawings, of which.

DESCRIPTION OF THE PREFERRED EMBODIMENT

Figure 1:
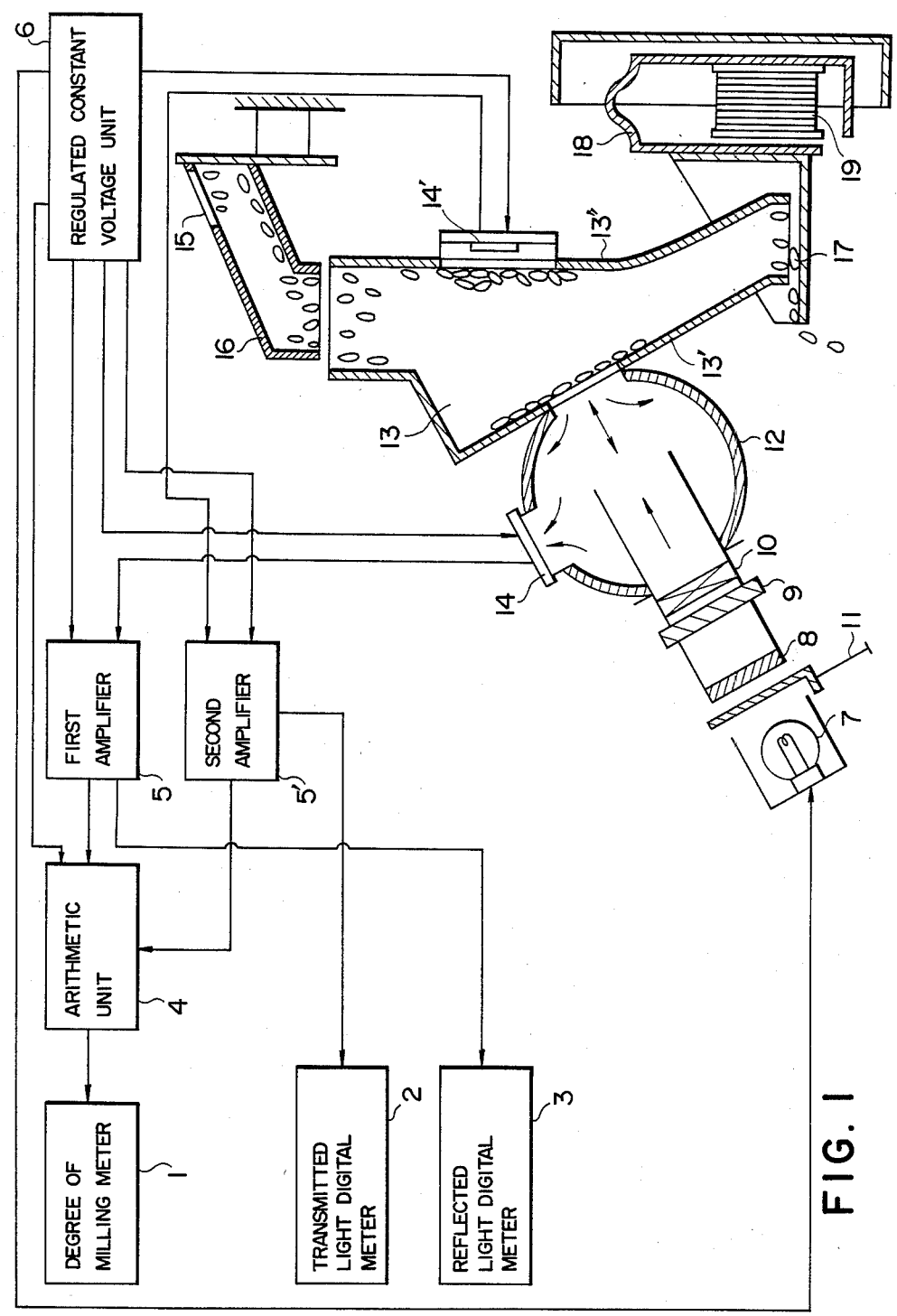
FIG. 1 is a diagrammatic view showing an embodiment of the invention.

Referring now to the drawings, a first embodiment of the invention is shown in FIG. 1.

Reference numeral 12 indicates an integrating sphere the inner surface of which is of a mirror finish, at the right side of which there is arranged a grain passage unit 20 or a grain passage 13, and at the left side of which there is arranged a condenser lens 10. At the left side of the condenser lens 10, there are arranged a light source lamp 7, an infrared filter 8 and a monochromatic light filter 9. Thus, a light source unit is formed by the light source lamp 7, the infrared filter 8, the monochromatic light filter 9 and the condenser lens 10. Reference numeral 11 indicates a shutter.

Above the grain passage 13 there is provided a grain chute 16 having a grain feeding opening 15, and at the lower end of the grain passage 13 there is arranged a vibration plate 17 in spaced relation with the end of the grain passage. This vibration plate 17 is carried by a vibrator 18. Reference numeral 19 indicates an electromagnet. The amount of the grains flowing in the grain passage 13 is controlled by the adjustment of the vibration frequency of the vibration plate 17, that is, the adjustment of the vibration frequency of the vibrator 18.

The grain passage unit 13 is disposed in the path of the light from the light source lamp 7 and has at the side of the light source unit a first wall 13' which is angularly positioned with an angle sufficient to allow the grains to slide downwardly thereon but smaller than the vertical angle, that is, with an angle appropriate for the grains in contact with the wall slide down with their lengthwise axes generally parallel to the wall surface. The grain passage 13 is formed like a hopper with the passage becoming progressively narrower toward the end thereof. A second wall 13'' of the grain passage 13 is positioned opposite to the first wall 13' and at the far side from the light source such that the grains which are introduced in the passage 13 flow without a gap between this second wall 13'' and the grains. Thus, the second wall 13'' is preferably vertical rather than, for example, parallel to the angularly positioned first wall 13' in which case there may occur a gap between the second wall and the grains.

At the portion of the integrating sphere 12 on a line perpendicularly crossing the line between the light source unit and the transmitted light sensing element 14', there is provided a reflected light sensing element 14 which receives the light reflected by the grains and which is connected to a first amplifier 5. At the second wall 13'' of the grain passage 13, there is provided a transmitted light sensing element 14' which receives the light transmitted through the grains and which is connected to a second amplifier 5'.

The first amplifier 5 and the second amplifier 5' are connected to an arithmetic element 4 serving as an arithmetic unit, which is in turn coupled to a degree of milling meter 1 which in this embodiment is constituted by a digital display.

In the drawing, reference numeral 2 indicates a transmitted light digital meter connected to the second amplifier 5', reference numeral 3 indicates a reflected light digital meter connected to the first amplifier 5 and reference numeral 6 indicates a regulated constant voltage unit.

Thus, the integrating sphere 12, the reflected light sensing element 14 and the first amplifier 5 constitute a reflected light detecting unit and the transmitted light sensing element 14' and the second amplifier 5' constitute a transmitted light detecting unit.

In the construction as described above, the value, that is, the degree of milling of rice grains calculated at the arithmetic unit 4 based upon both the value from the first amplifier 5 corresponding to the amount of the reflected light and the value from the second amplifier 5' corresponding to the amount of the transmitted light, can be expressed by the following equation:

$$\text{Degree of milling of grains} = \frac{\text{amount of reflected light}}{K \cdot \text{amount of transmitted light}}$$

In the above equation, K is a coefficient (using an empirical value) for converting the degree of transmitted light into the degree of milling.

As has been described above, according to the present invention, since the degree of milling of grains is derived from the sum of the reflection degree and the transmission degree of the light, the degree of milling thereof can be measured with accuracy even in the case of well milled rice grains having smooth surfaces. Moreover, since the first wall, which is the one located at the near side from the light source unit, of the grain passage is positioned angularly with an angle to allow the grains in contact with the wall to slide downwardly thereon with their lengthwise axes oriented generally parallel to the wall surface, thus ensuring the accurate and constant measurement of the value of the reflected light. Also, since the second wall which is the one located at the far side from the light source unit is positioned so that the grains flow without a gap between this wall and the grains, this ensures the accurate measurement of the value of the transmitted light.

Figure 2:
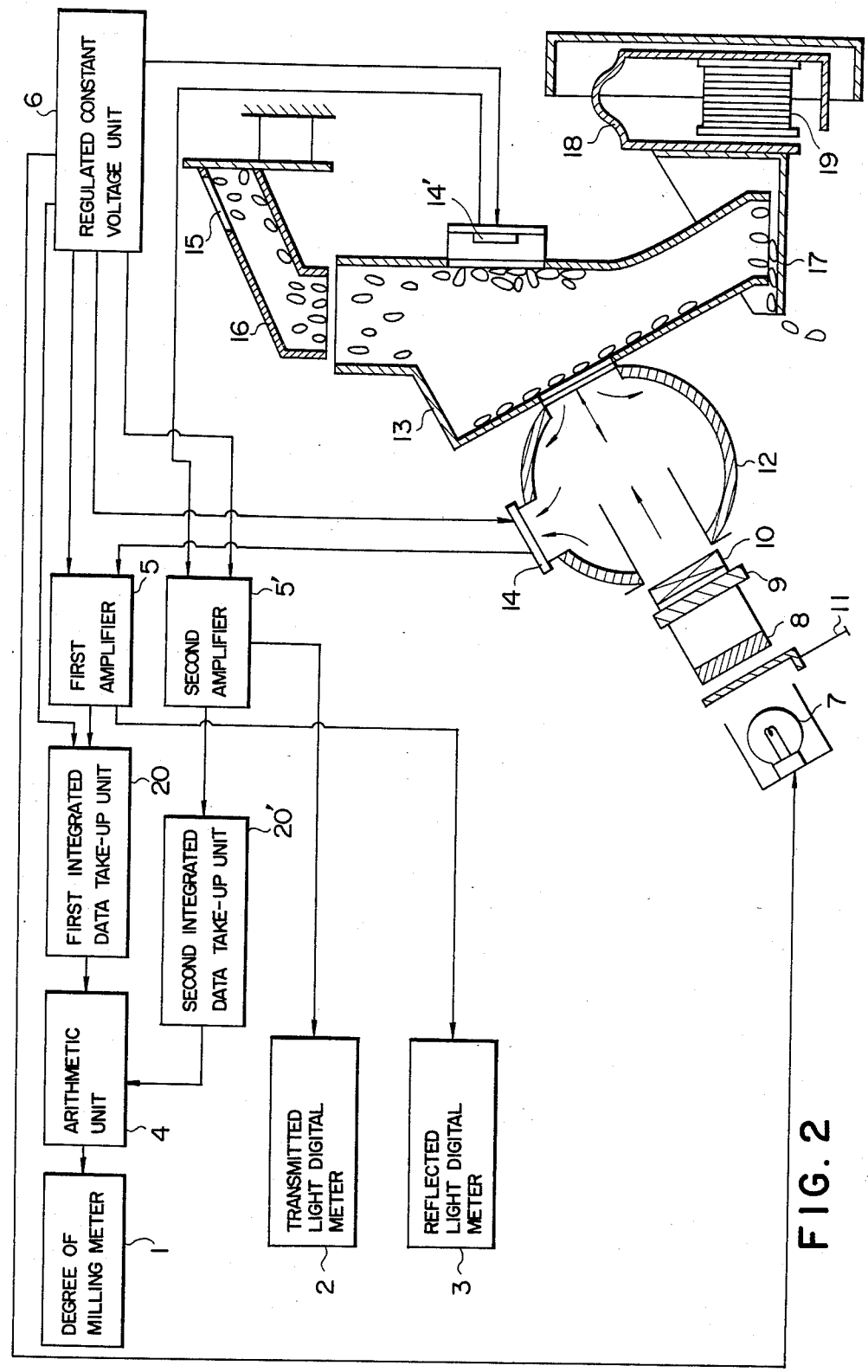
FIG. 2 is a diagrammatic view showing another embodiment of the invention.

The second embodiment of the present invention is shown in FIG. 2 wherein like reference characters designate like or corresponding parts and function as in FIG. 1.

In this second embodiment, the first amplifier 5 and the second amplifier 5' are coupled to the arithmetic unit 4 through a first integrated data take-up unit 20 and a second integrated data take-up unit 20', respectively, and further coupled to the degree of milling meter 1.

Figure 3:
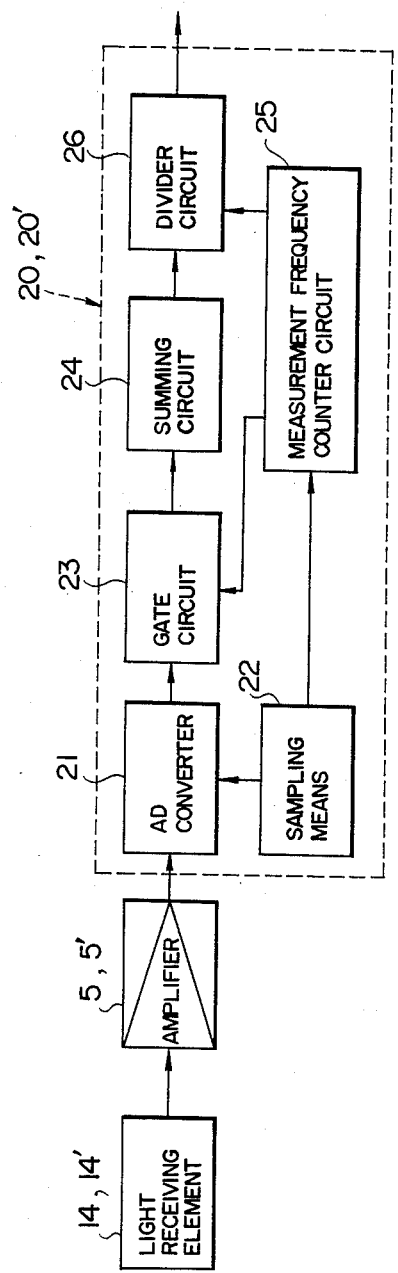
FIG. 3 is a block diagram of an integrated data take-up unit shown in FIG. 2.
Figure 4:
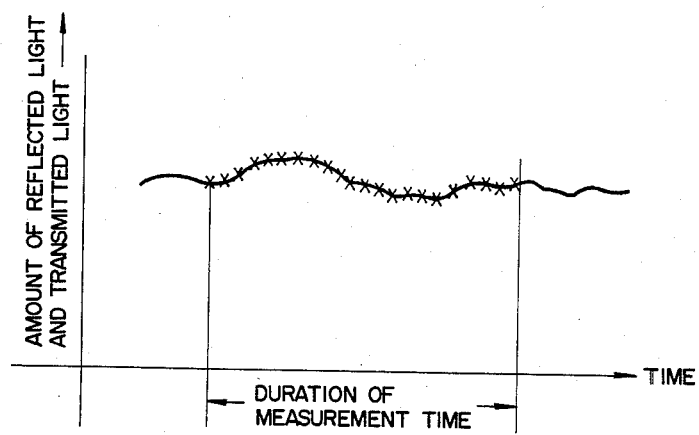
FIG. 4 is a graph showing a variation in the amount of the reflected and transmitted light in relation to the progress of time.

As shown in FIG. 3, each of AD converters 21 in the first and second integrated data take-up units 20 and 20' is connected to each of the outputs of the first and second amplifiers 5 and 5', and is subjected to a sampling operation every 0.1–0.5 seconds by a sampling means 22. The output value of the AD converter 21 is then forwarded to a summing circuit 24 via a gate circuit 23.

On the other hand, a sampling signal generated at the sampling means 22 is also applied to a measurement frequency counter circuit 25 where the number of times the measurement has occured is counted. The number of times thus counted is applied to the gate circuit 23 and also a divider circuit 26. The output of the summing circuit 24 is input to the divider circuit 26 and the output of this divider circuit 26 is in turn input to the arithmetic unit 4 in the form of integrated data.

Then, after analogue values each of which corresponds to the amount of the reflected light and the transmitted light obtained by the light sensing elements 14 and 14' are amplified by the first and second amplifiers 5 and 5', they are subjected to a sampling operation at each predetermined period of time by the sampling means 22, and then converted to a digital value by the AD converter 21 and are forwarded to the gate circuit 23.

The measurement frequency counter circuit 25 counts the number of times or frequency of the sampling means 22 and then outputs a certain number of times of counting per predetermined duration of measurement time.

The digital value, which corresponds to the amount of the reflected light or the transmitted light and which is passing through the gate circuit 23 after the commencement of the counting operation of the measurement frequency counter circuit 25, is summed successively at the summing circuit 24 and then forwarded to the divider circuit 26. At this divider circuit 26, the digital value sent from the summing circuit 24 is divided by the number of times which is counted until a counter-stop signal is sent from the measurement frequency counter circuit 25, that is, by the duration of measurement time, and an averaged value thus obtained within this measurement time is forwarded to the arithmetic unit 4 in the form of integrated data.

As has been mentioned above, in the apparatus according to the present invention in which the integrated data take-up units are provided for the arithmetic unit and the degree of milling meter, since the degree of milling of rice grains is represented as an averaged value of the consecutively measured values over the predetermined period of time, a more accurate degree of milling without fluctuations can be obtained as compared with the one calculated only based upon the sum of the amount of the reflected light and the transmitted light.

While the invention has been described in its preferred embodiments, it is to be distinctly understood that the invention is not limited thereto but may be otherwise variously embodied within the scope of the following claims.

What is claimed is:

1. An apparatus for continuously measuring the degree of milling of grains comprising
    a light source unit directing light to be reflected by and transmitted through the grains,
    a grain passage unit disposed in the path of said light and having a first wall disposed at the near side from said light source unit and a second wall disposed at the far side from said light source unit,
    a reflected light detecting unit having a reflected light sensing element positioned adjacent to said first wall,
    a transmitted light detecting unit having a transmitted light sensing element adjacent to said second wall,
    an arithmetic unit connected to said reflected light detecting unit and said transmitted light detecting unit, and
    a degree of milling meter connected to said arithmetic unit,
    said first wall of said grain passage unit being positioned angularly so that the grains in contact therewith slide down with their lengthwise axes generally parallel to the wall surface and said second wall of said grain passage unit being positioned so that the grains which are introduced in said grain passage unit flow without a gap between the second wall and the grains.

2. An apparatus for continuously measuring the degree of milling of grains according to claim 1 wherein said reflected light detecting unit includes an integrating sphere and a first amplifier connected to said reflected light sensing element.

3. An apparatus for continuously measuring the degree of milling of grains according to claim 1 wherein said transmitted light detecting unit includes a second amplifier connected to said transmitted light sensing element.

4. An apparatus for continuously measuring the degree of milling of grains comprising
    a light source unit directing light to be reflected by and transmitted through the grains,
    a grain passage unit disposed in the path of said light and having a first wall disposed at the near side from said light source unit and a second wall disposed at the far side from said light source unit,
    a reflected light detecting unit having a reflected light sensing element positioned adjacent to said first wall,
    a transmitted light detecting unit having a transmitted light sensing element adjacent to said second wall,
    an arithmetic unit connected to said reflected light detecting unit and said transmitted light detecting unit,
    a degree of milling meter connected to said arithmetic unit,
    a first integrated data take-up unit connected to said reflected light detecting unit, and
    a second integrated data take-up connected to said transmitted light detecting unit,
    said first integrated data take-up unit and said second integrated data take-up unit being connected to said degree of milling meter through said arithmetic unit whereby the integrated data obtained in a given period divided into a number of divisions is averaged to calculate the degree of milling being sought.

* * * * *